United States Patent
Lee et al.

(10) Patent No.: US 7,429,662 B2
(45) Date of Patent: Sep. 30, 2008

(54) RED-EMITTING ELECTROPHOSPHORESCENT DEVICES

(75) Inventors: Shuit Tong Lee, Hong Kong (CN);
Chun Sing Lee, Hong Kong (CN);
Baoxiu Mi, Hong Kong (CN); Peng-Fei Wang, Beijing (CN)

(73) Assignee: City University of Hong Kong, Hong Kong (CN)

( * ) Notice: Subject to any disclaimer, the term of this patent is extended or adjusted under 35 U.S.C. 154(b) by 0 days.

(21) Appl. No.: 11/133,664

(22) Filed: May 20, 2005

(65) Prior Publication Data
US 2006/0261730 A1 Nov. 23, 2006

(51) Int. Cl.
*C07F 11/00* (2006.01)
*B32B 9/00* (2006.01)
*B32B 19/00* (2006.01)

(52) U.S. Cl. .................................. 544/225; 428/690
(58) Field of Classification Search .................. 544/225
See application file for complete search history.

(56) References Cited

U.S. PATENT DOCUMENTS 5,935,720 A 8/1999 Chen et al.
6,821,645 B2 * 11/2004 Igarashi et al. .............. 428/690

OTHER PUBLICATIONS

Tang and VanSlyke. Applied Physics Letters, 51, 913 (1987).
Shirota, Y. J Material Chem., 10, 1-25 (2000).
Chen, Shi and Tang. Macromolecular Symposia, 125, 1(1997).
Mitschke, U. and Bauerle, P. Journal of Material Chemistry, 10, 1471-1507 (2000).
Lamansky, S.; Djurovich, P.; Murphy, D.; Abdel-Razzaq, F.; Lee, H.-E.; Adachi, C.; Burrows, P.E.; Forrest, S.R.; Thompson, M.E., Journal of Am. Chem. Soc., 123, 4304 (2001).
Su, Y.-J.; Huang, H.-L.; Li, C.-L.; Chien, C.-H.; Tao, Y.-T.; Chou, P.-T.; Datta, S.; Liu, R.-S.; Advance Materials, 15, 884 (2003).
Duan, J.-P.; Sun, P.-P.; Cheng, C.-H. Advanced Materials, 15, 224 (2003).

* cited by examiner

*Primary Examiner*—Mark L. Berch
*Assistant Examiner*—Cecilia M Jaisle
(74) *Attorney, Agent, or Firm*—Heslin Rothenberg Farley & Mesiti P.C.; Charles E. Bell, Esq.

(57) ABSTRACT

This invention relates to an organic electroluminescence (EL) device and to the use of a tris-cyclometalated iridium complex with a 3-Phenyl-azine ligand for thin-film type organic electroluminescence devices.

The iridium complexes used have the following formulae:
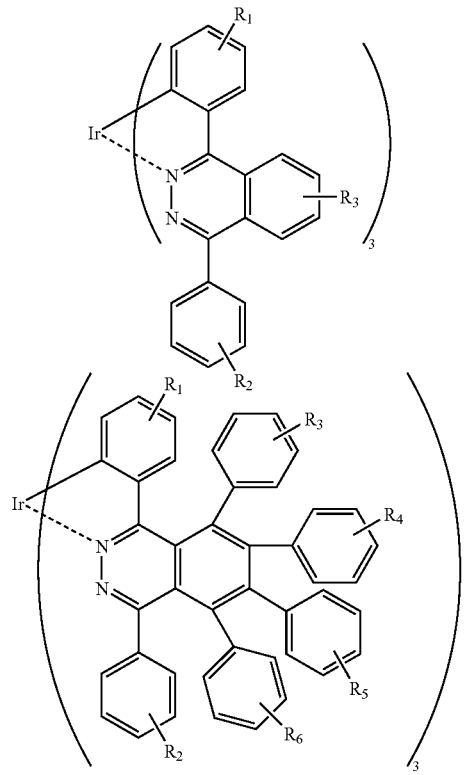
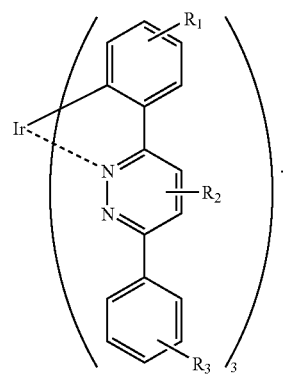
3 Claims, 7 Drawing Sheets

RED-EMITTING ELECTROPHOSPHORESCENT DEVICES

FIELD OF THE INVENTION

This invention relates to an organic electroluminescence (EL) device and to the use of a tris-cyclometalated iridium complex with a 3-Phenyl-azine ligand for thin-film type organic electroluminescence devices.

BACKGROUND

Historically, the efficiencies and lifetimes of organic electroluminescence ("EL") devices were much lower than those obtained from inorganic systems. Therefore, research mainly focused on inorganic materials.

The reason for the low luminance of the early organic EL device is the highly resistive EL medium, which prevents the efficient injection of carriers into the light-emitting layer. Tang and VanSlyke addressed this problem in the late 1980s (Tang and VanSlyke, Appl. Phys. Lett. 1987, 51, 913) by using a structure made of two ultra thin layers: a hole transporting layer of an organic substance laminated on an organic emitting layer. This work revived the research on organic EL devices, and resulted in the development of a new generation of light-emitting diodes with organic dyes. One of the most convenient and useful methods is to dope a strong emitting material into a host material to form a guest-host system. Thus, in principle, an organic EL device with good efficiency and high stability, as well as desired color with proper chromaticity, can be obtained by doping different strongly emitting materials into a host material such as tri-(8-hydroxyquinolinato)aluminum ($Alq_3$) to meet the requirement of the practical applications. As a general rule, the energy gap between the lowest unoccupied molecular orbital (LUMO) and the highest occupied molecular orbital (HOMO) of a host material should be larger than that of the doped guest material to allow an efficient energy transfer from the host to guest.

Light emission from OLEDs is typically via fluorescence or phosphorescence. For OLEDs based on fluorescent materials, only a small percentage (about 25%) of excitons in fluorescent devices are capable of producing the fluorescent luminescence that is obtained from a singlet-excited state. The remaining excitons in a fluorescent device, which are produced in the lowest triplet excited state of an organic molecule, are typically not capable of being converted into the energetically unfavorable higher singlet excited states from which the fluorescence is produced. This energy would be lost via non-radiative decay processes that only tend to heat-up the device. An efficient way to tape the other 75% excitons for light emission is to use materials in which the triplet excited state can decay to the ground state efficiently in radiative way, i.e. phosphorescence. The advantage is that all excitons, either in singlet or triplet excited states, may participate in luminescence. This is because the lowest singlet excited state of an organic molecule is typically at a slightly higher energy than the lowest triplet excited state. This means that, for typical phosphorescent organometallic compounds, the lowest singlet excited state may rapidly decay to the lowest triplet excited state from which the phosphorescence is produced. For this reason, there is much interest in finding efficient electrophosphorescent materials and OLED structures containing such materials, especially those emitting in saturated red.

It would therefore be desirable to provide an improved or alternative compound for use in organic light emitting devices that overcomes the problems associated with the prior art.

SUMMARY OF THE INVENTION

In a first aspect, the invention broadly describes an organic compound according to one of formulae (I)-(III).

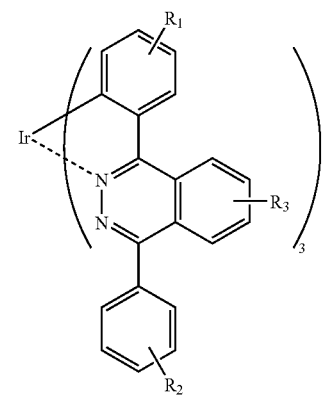

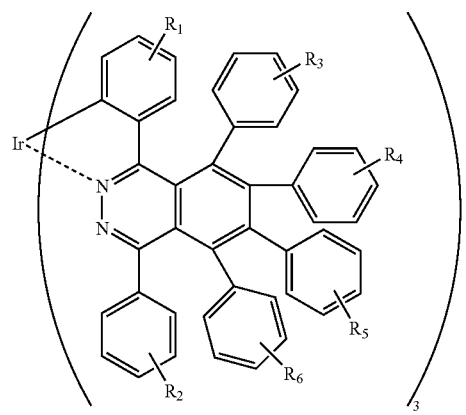

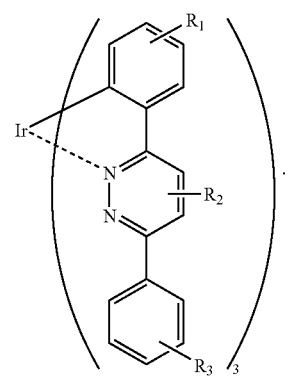

In each of formulae (I)-(III), each $R_1$-$R_6$ is selected independently from the groups consisting of hydrogen, halogen, cyano, nitro, alkyl, alkylamino, dialkylamino, arylamino, diarylamino, haloalkyl containing a lower alkyl, hydroxyalkyl containing a lower alkyl, styryl, alkyloxy, alkylthio, aryloxy, arylthio, siloxy, aryl, substituted aryl, substituted heterocycle, or unsubstituted heterocycle.

"Alkyl" refers to saturated hydrocarbon residues containing eighteen or fewer carbons in straight or branched chains, as well as cyclic structures.

"Lower alkyl" refers to those containing from 1-4 carbon atoms.

"Aryl" refers to an aromatic hydrocarbon of 4 to about 16 carbon atoms.

The term "heterocycle" includes an unsaturated cyclic residue with 1-16 carbon atoms and from 1-4 heteroatoms selected from the group comprising nitrogen, oxygen and sulfur.

Examples of suitable alkyl groups containing from 1-18 carbon atoms include methyl, ethyl, propyl, butyl, sec-butyl, tert-butyl, pentyl, hexyl, heptyl, octyl, and stearyl.

Examples of alkyl amino residues include methyl amino, ethyl amino, propyl amino, butyl amino, sec-butyl amino, tert-butyl amino, pentyl amino, hexyl amino, heptyl amino, octyl amino, and stearyl amino.

Examples of dialkylamino groups include dimethyl amino, diethyl amino, dipropyl amino, dibutyl amino, disec-butyl amino, ditert-butyl amino, dipentyl amino, dihexyl amino, diheptyl amino, dioctyl amino, and distearyl amino.

Phenyl amino is a preferred arylamino.

Examples of diarylamino groups include diphenyl amino, phenylnaphthylamino, phenylanthrylamino, o-, p-, m-tolylnaphthylamino, o-, p-, m-tolylanthrylamino, or naphthylanthrylamino.

Examples of lower haloalkyl groups include chloromethyl, 3-chloropropyl, dichloromethyl, trichloromethyl, fluoromethyl, difluoromethyl, and trifluoromethyl.

Lower hydroxyalkyl residues include hydroxymethyl, hydroxyethyl, and hydroxypropyl.

Alkyloxy groups, also referred to as "alkoxyl", include methoxy, ethoxy, propoxy, butoxy, sec-butoxy, tert-butoxy, and stearyloxy.

Phenyloxy is a preferred aryloxy residue.

Examples of alkylthio substituents include methylthio, ethylthio, propylthio, butylthio, sec-butylthio, and tert-butylthio.

Phenylthio is an example of an arylthio group.

Examples of substituted or unsubstituted aryl groups containing only monocyclic hydrocarbons include phenyl, biphenylyl, triphenylyl, o, m-, p-tolyl, xylyl, o-, m-, p-cumenyl, mesityl, and similar such compounds.

Exemplary fused polycyclic aryl group, substituted or unsubstituted, include pentalenyl, indenyl, naphthyl, azulenyl, heptalenyl, acenaphthylenyl, phenalenyl, fluorenyl, anthryl, anthraquinonol, phenanthrolyl, pyrenyl, chrysenyl, picenyl, rubicenyl, trinaphthylenyl, pyranthrenyl, ovalenyl, and similar such compounds.

"Heterocycles", substituted or unsubstituted, may include thienyl, furyl, pyrrolyl, imidazolyl, pyrazolyl, pyridyl, pyrazinyl, pyrimidinyl, pyridazinyl, indolyl, quinolyl, isoquinolyl, phthalazinyl, quinoxalynyl, quinazolynyl, carbazolyl, acridinyl, isothiazolyl, furazanyl, benzthiazolyl, benzoxazolyl, and benzoimidazolyl.

In a second aspect the invention broadly describes an organic electroluminescence device comprising an anode, a cathode, an electron layer and at least one organic emitting layer comprising a compound of any one of one of formulae (I), (II), or (III).

DETAILED DESCRIPTION OF THE INVENTION

Iridium-based metal complexes have been investigated for phosphorescent OLEDs for to the following reasons:

(i) Orthometalated iridium complexes are known to have the highest triplet quantum yields due to several factors:
  (a) Iridium has large d-orbital splitting compared to other metals in the series.
  (b) The strong ligand field strength of the phenyl anion ligand increases the energy separation between the $t_{2g}$ and $e_g$ orbitals, leading to an enhanced gap between the $e_g$ and LUMO of the ligand.
  (c) Close lying $\pi$-$\pi$* and MLCT states together with the heavy atom effect enhance the spin-orbit coupling.

(ii) The stable form of 3+ oxidation state Ir(III) can form neutral complexes to allow sublimation.

(iii) The octahedral configuration of iridium complexes results in small aggregation even at high doping concentrations compared to other metal-based complexes, such as platinum complexes in the form of a planar structure.

Iridium-complexes-based OLED materials emitting in blue, green and red have all been reported. However, red phosphorescent OLEDs are still the most challenging in terms of efficiency, color purity and stability. Phosphorescent red OLEDs with high efficiency and saturated red color are rare. Thus, EL device with a saturated red emission based on triscyclometalated iridium complexes with high chemical and thermal stability are very much in demand.

Electrophosphorescent OLEDs are typically comprised of several layers so as to achieve the desired combination of OLED performance characteristics. For example, high efficiencies in OLEDs may be obtained by differentiating the charge transport and luminescent functions between a host and guest material. A suitable host material may act as a good transporter of charge, as well as efficiently transferring energy to a highly luminescent guest.

The applicants have discovered that by using compounds of formulae I, II and III in the luminescent layer of OLEDs, said OLEDs exhibit improved performance with higher maximum external efficiency, a more saturated red color among all reported Ir complexes and the CIE color coordinates (x=0.69, y=0.30).

Figure 1:
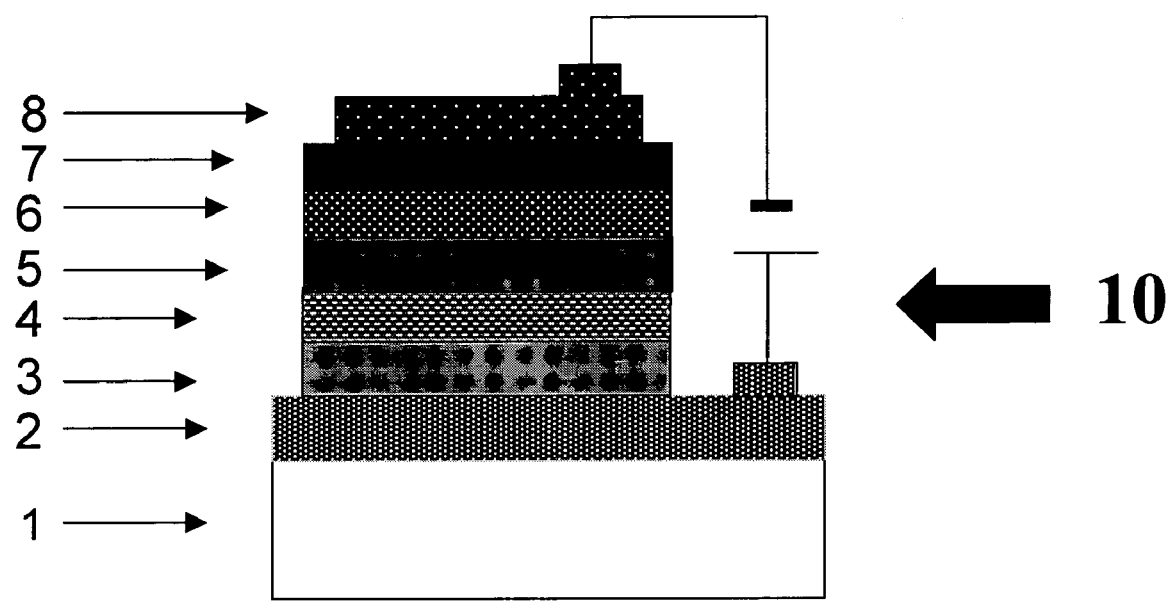
FIG. 1 shows a cross-sectional view of an organic electroluminescence device according to the present invention.

FIG. 1 illustrates a diagram of the organic electroluminescence device structure 10. As can be seen, the device comprises a substrate 1, an anode 2, an organic hole injection layer 3, an organic hole transport layer 4, an organic emitting layer 5, an organic hole blocking layer 6, an organic electron transport layer 7 and a cathode 8.

Figure 2:
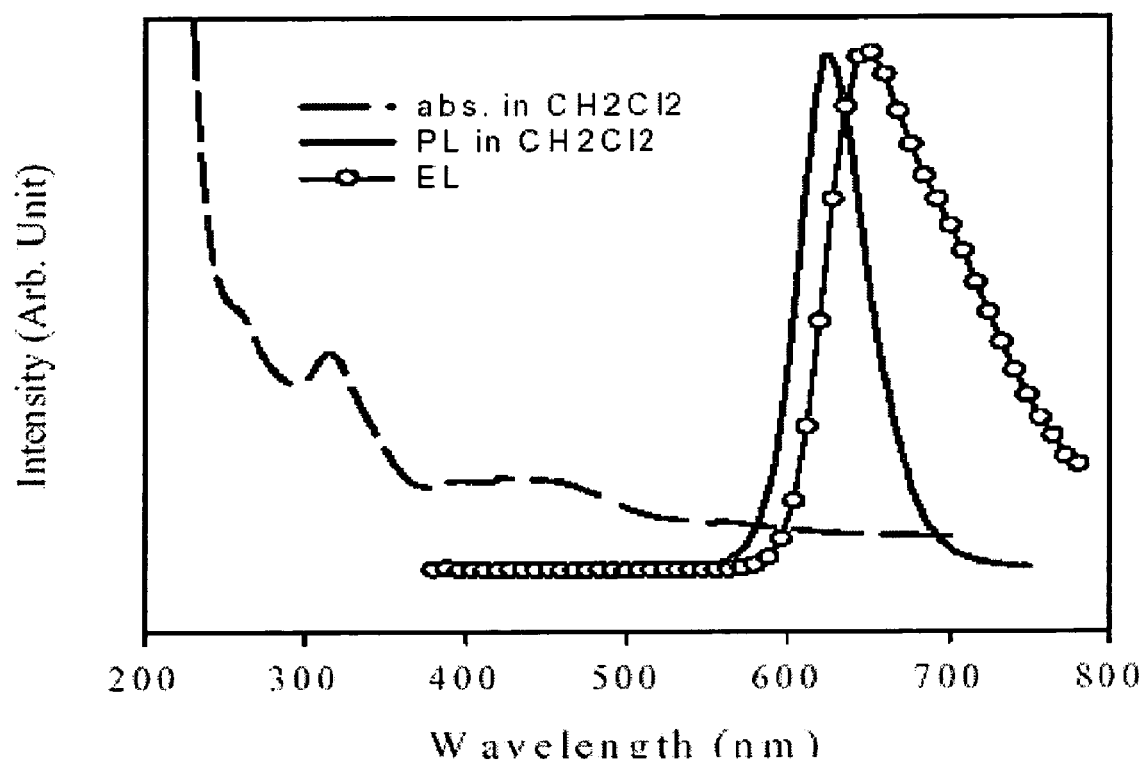
FIG. 2 is a diagram of UV and PL spectra of IrBPPa in $CH_2Cl_2$, and EL spectrum.

FIG. 2 is the absorption, PL spectra of IrBPPa in CH2Cl2, and EL spectrum with the device configuration of ITO/NPB (15 nm)/NPB:0.5%IrBPPa (5 nm)/CBP:5%IrBPPa (20 nm)/TPBI (10 nm)/AlQ3 (40 nm). The PL spectra of IrBPPa in dilute solution (peaked at 625 nm), the EL spectra show a maximum emission at 648 nm with a large long wavelength tail. A red shift of 23 nm is observed. This is most likely caused by high doping concentration (5%). The fact that such a tail does not exist even in the film of IrBPPa (not shown) infers that IrBPPa might form exciplex with the host CBP or with the adjacent TPBI. The tail may also be the result of differences in distortions that the complex can undergo in the different environments. Given better device configuration to eliminate the tail, the efficiency of the red device can be expected to further improve.

Figure 3:
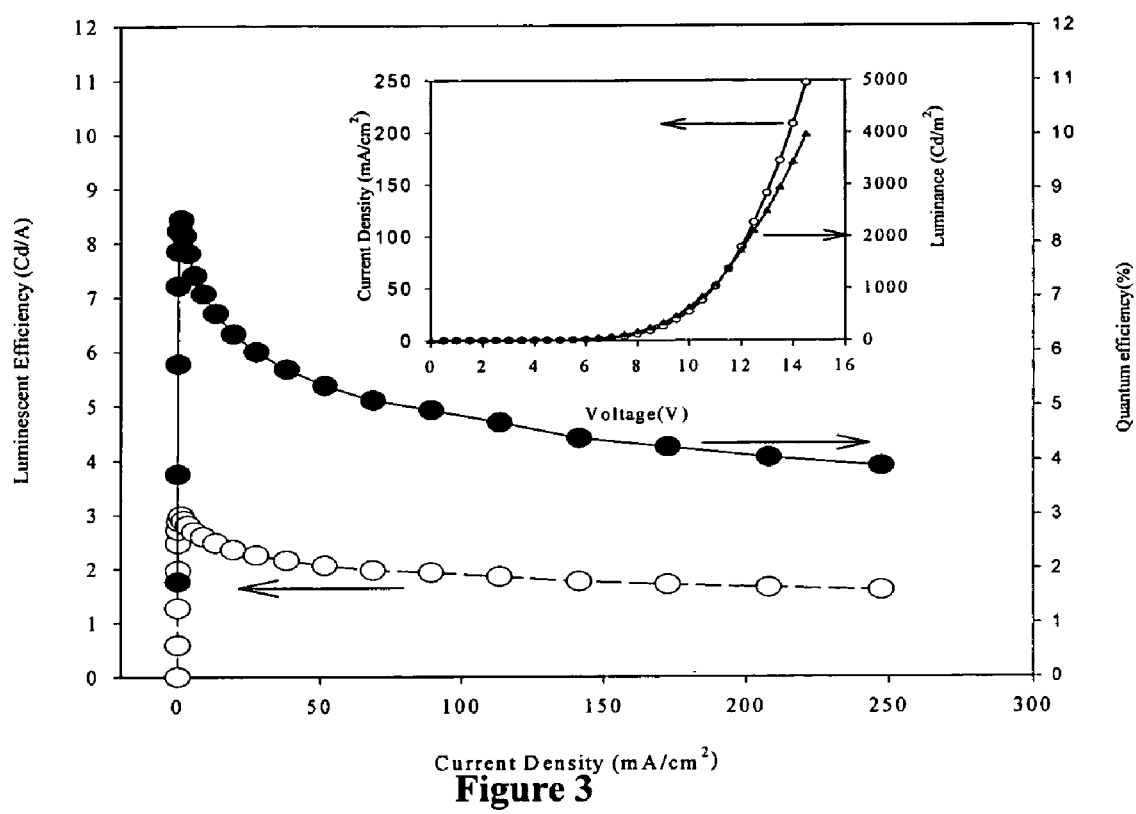
FIG. 3 is a plot of external quantum efficiency and current efficiency of the device. (Inset: I-V-B characteristics).

FIG. 3 shows the EL performance of device with configuration of ITO/NPB (15 nm)/NPB:0.5%IrBPPa (5 nm)/CBP:5%IrBPPa (20 nm)/TPBI (10 nm)/AlQ3 (40 nm). Very high performance of red phosphorescence was achieved. The device has a maximum external efficiency of 8.43%, a current efficiency of 3.0 cd/A at a driving voltage of 6.5 V. Even at high current density of 200 mA/cm2, the efficiency of the device remains extraordinarily high at 4.24% and 1.7 cd/A at 13.5 V.

Figure 4:
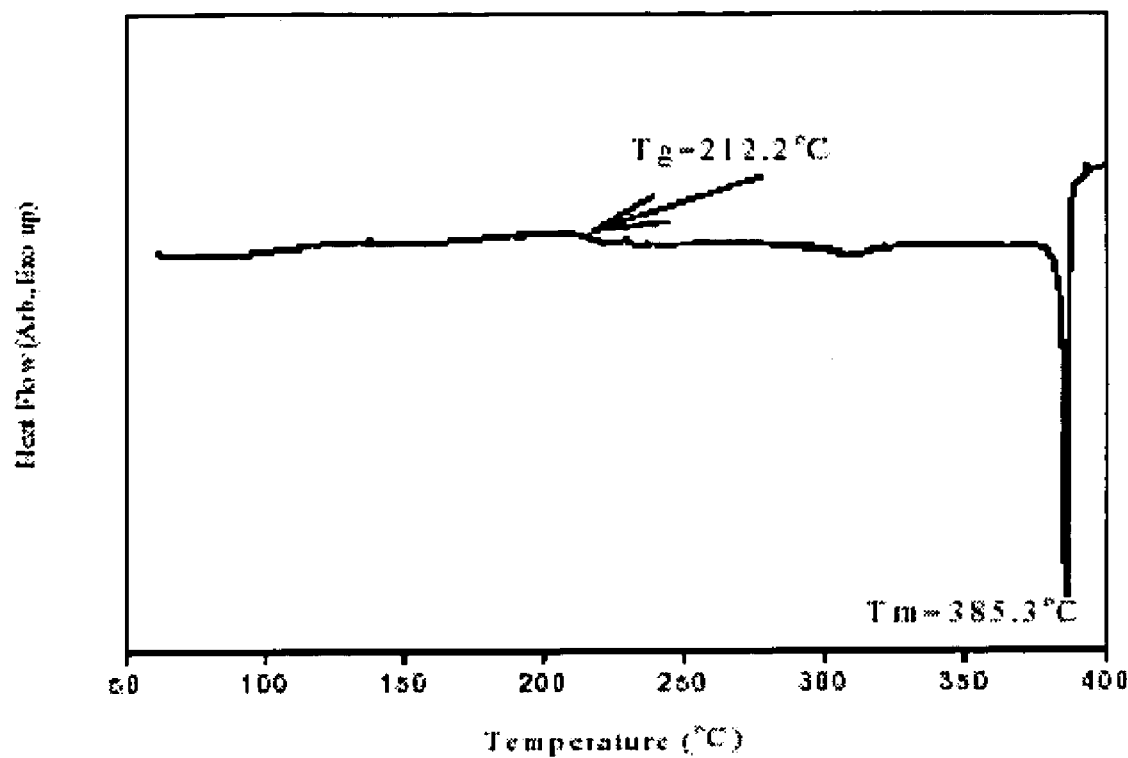
FIG. 4 is a plot of the DSC curve of IrBPPa.

FIG. 4 is DSC curve of IrBPPa. Very high Tg and Tm indicate good thermo-stability of the present Ir-complexes.

Figure 5:
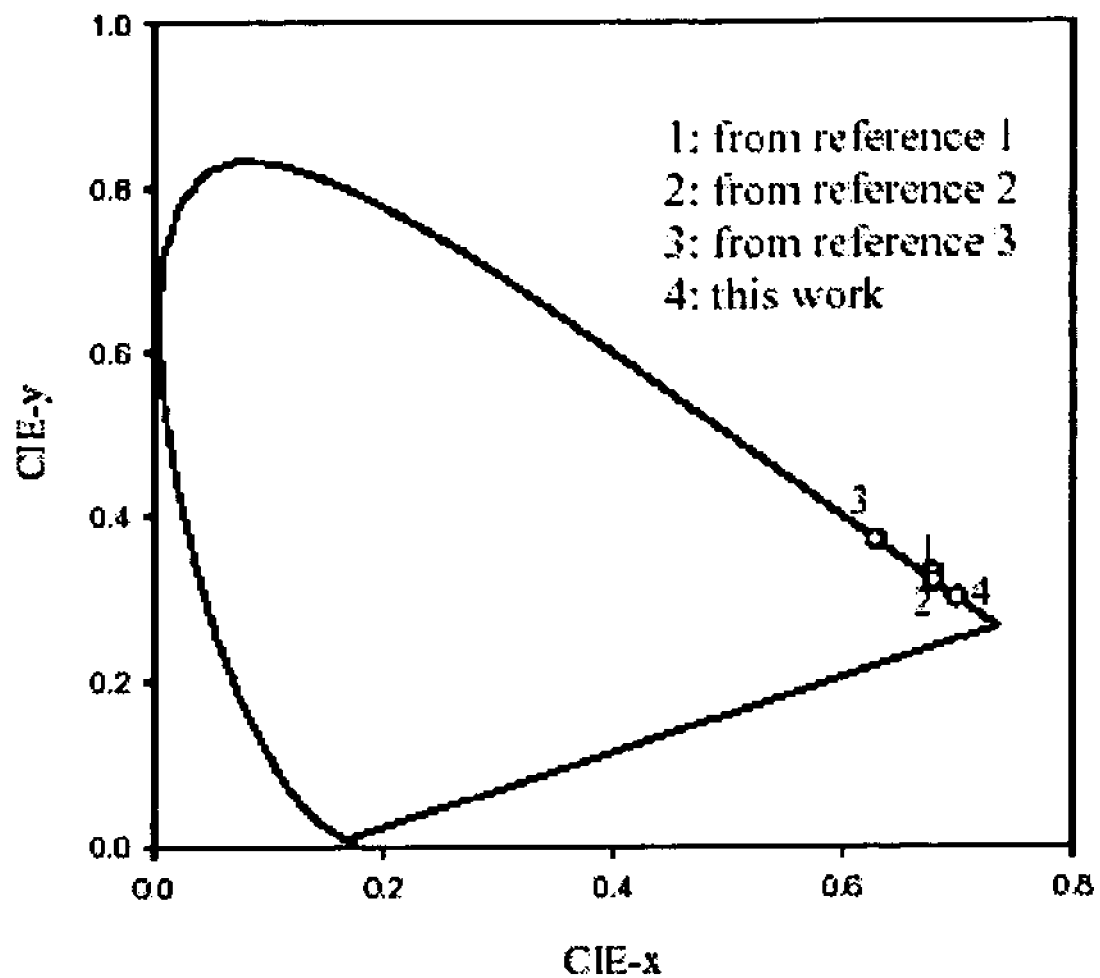
FIG. 5 is a plot of CIE color coordinates among the works shown in table 1.

FIG. 5 shows the comparison of CIE coordinates with the state-of-the-art red electrophosphorescent device. It gave the most saturated red color among all reported Ir complexes and the Commission Internationale de L'Eclairage (CIE) color coordinates (x=0.69, y=0.30) remain constant over a wide range of driving voltages from 0 to 15 V.

Figure 6:
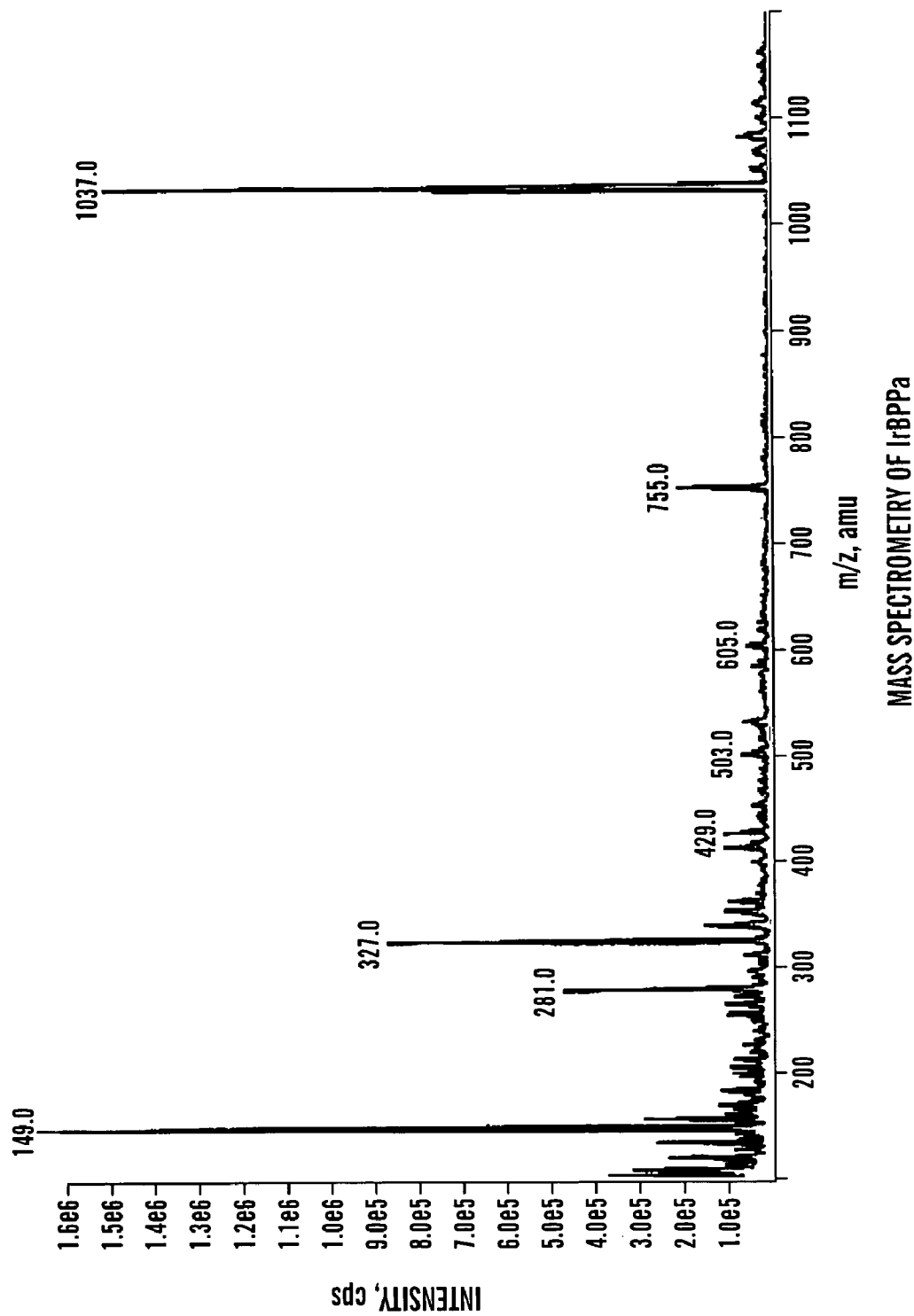
FIG. 6 is a diagram of the mass spectrometry of IrBPPa.
Figure 7:
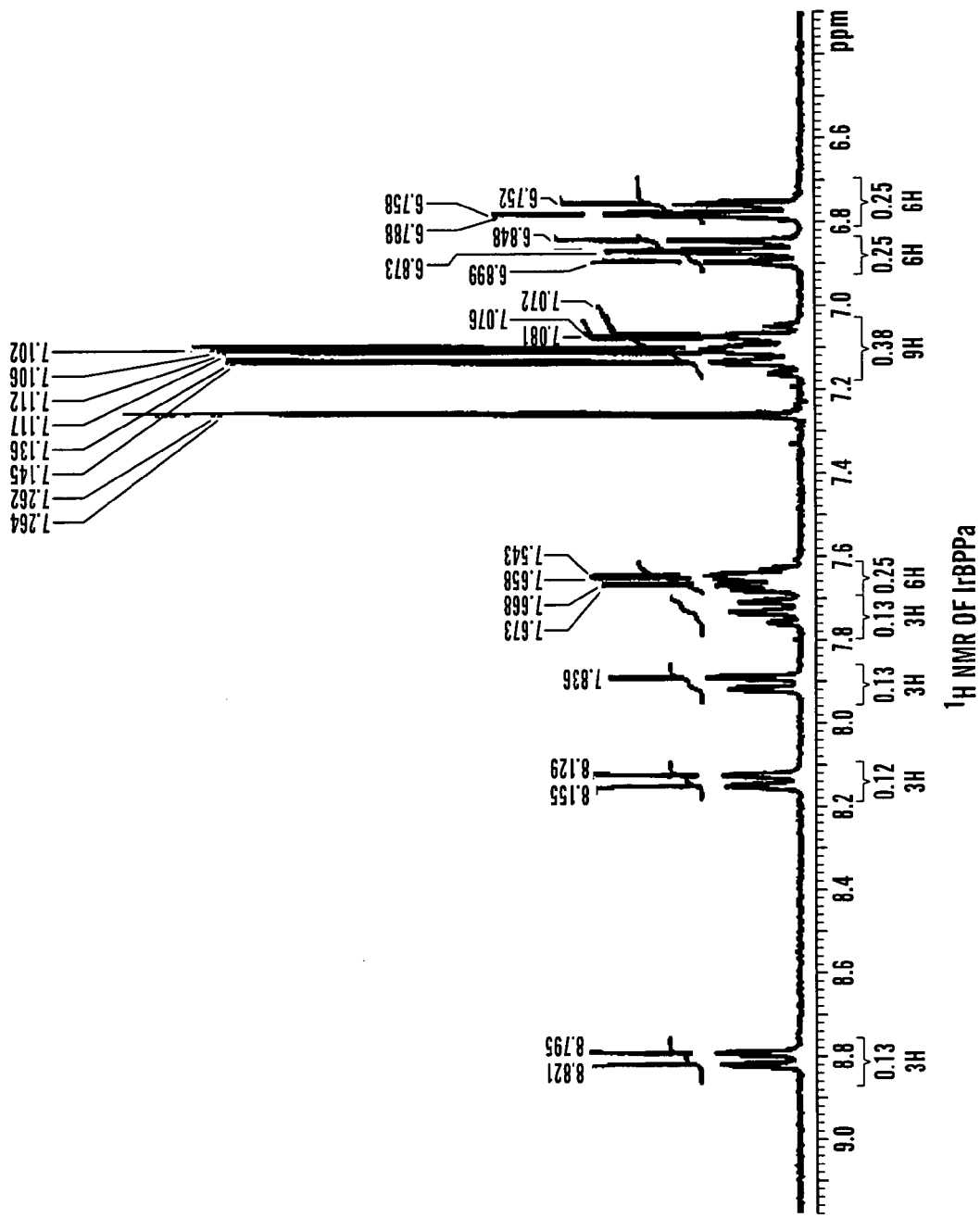
FIG. 7 is a diagram of $^1H$ NMR of IrBPPa.

FIGS. 6 and 7 show the mass spectrometry and $^1$H NMR of IrBPPa, respectively.

With reference to FIG. 1, the substrate 1 is used as a support for the organic electroluminescence device of the present invention. Examples of useful substrates that would be known to a person skilled in the art are a quartz or glass sheet, a metal sheet or foil, or a plastic film or sheet. Preferred materials are a glass sheet or transparent synthetic resin, such as polyester, polycarbonate, and polysulfone.

An anode 2 is located on the substrate 1. It can be made of a metal such as silver, gold, aluminum, nickel, palladium, a metal oxide such as an oxide of indium and/or tin, carbon black or a conductive resin such as poly(3-methylthiophene). The materials mentioned above for making the anode may also be employed in preparing a cathode. However, the preferred material for a cathode is a metal with low work function, which is conducive to the efficient injection of electrons. Thus, a suitable metal such as magnesium, aluminum, silver, indium, or their alloys may be used.

The method for preparing the anode and the cathode is vacuum deposition or sputtering generally. However, when the material is the form of fine particles of a metal, carbon black, a metal oxide or conductive resin powder, it can be dispersed into a suitable binder resin in solution and coated on a substrate to form the electrodes. Furthermore, in the case of a conductive resin, a thin film may be formed directly on a substrate by electrolytic polymerization.

The anode or cathode can be made to have a multilayered structure by depositing the different materials mentioned above. However, at least one of the electrodes must transmit visible light to a required degree: preferably at least 60%, and more preferably at least 80%. To achieve this, the thickness of the layer is generally from 5 to 1,000 nm, preferably from 10 to 500 nm.

The hole injection layer 3 is introduced between the anode and the hole transport layer ("HTL"). A layer of hole-injection material (sometimes referred to as ITO or anode buffer layer) which reduces the energy barrier in-between ITO/HTL is therefore beneficial to enhancing charge injection at the interfaces and ultimately improving power efficiency of the device. Thus, hole-injection can be promoted by introduction of new hole-transport layers with optimized HOMO levels and by inserting a thin layer of copper phthalocyanine (CuPc), starburst polyamines, polyaniline and $SiO_2$ between the ITO/HTL interface. In addition, HTLs doped with oxidizing agents such as $FeCl_3$, iodine, tetra(fluoro)-tetra(cyano) quinodimethane (TF-TCNQ) and tris(4-bromopheny-1) aminium hexachloroantimonate (TBAHA) have been reported as effective materials for hole-injection. As examples, materials known to be useful as hole injection materials, either combined or separately, are illustrated as follows:

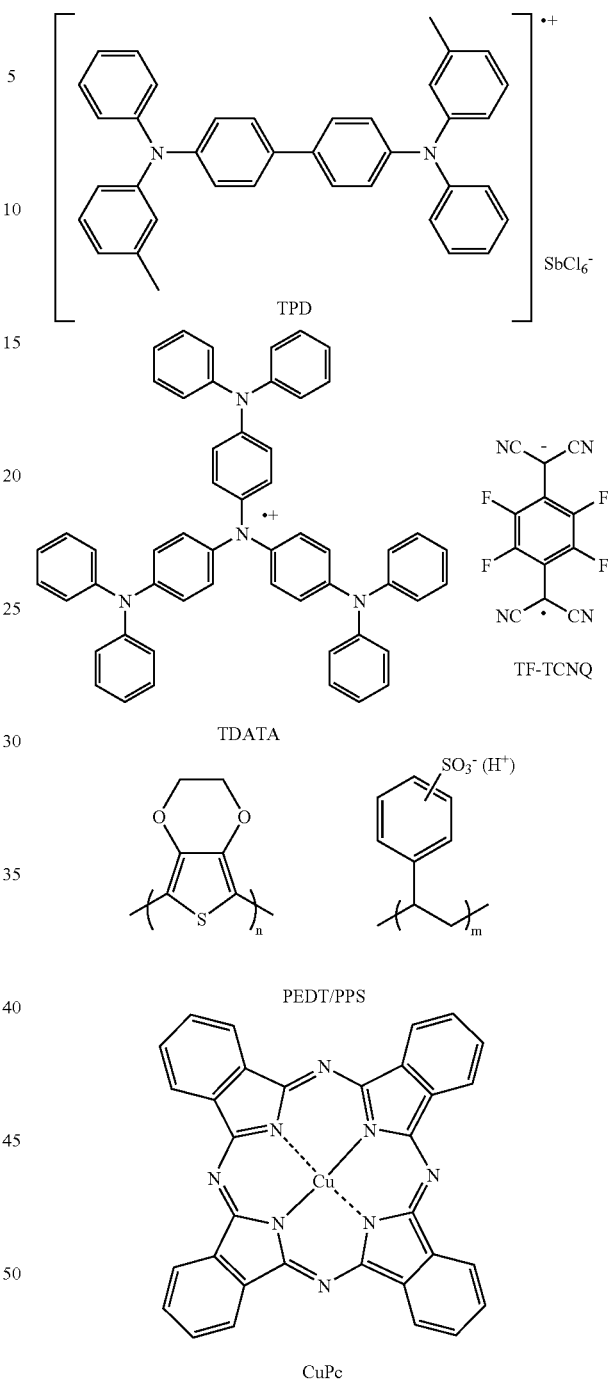

This hole injection layer 3 will typically have a thickness of from 5 to 400 nm, preferably from 10 to 50 nm.

An organic hole-transporting layer 4 is located on an anode. It generally consists of a compound that is able to transport holes efficiently from the anode to the organic emitting layer between the electrodes to which an electric field is applied. Therefore, such a compound is preferably highly efficient at injecting holes from the anode. It must be capable of efficiently transporting the injected holes to an emitting layer or an emitting material, preventing the migration of excitons generated in an emitting layer into an electron injecting zone or an electron transporting material, and highly capable of forming a thin film. Thus, in this respect, a suitable hole-transporting compound usually preferably has a low ionization potential, large hole mobility and stability. Moreover, the impurities likely to form traps should be avoided as far as possible.

Materials known to be useful as hole transporting materials, either combined or separately, include those disclosed in U.S. Pat. No. 5,935,720, phthalocyanine derivatives, naphthalocyanine derivatives, porphyrin derivatives, pyrazoline derivatives, carbazole derivatives, polymer materials such as polyvinylcarbazole, polysilane.

In the organic electroluminescence device of the present invention, effective hole transporting materials preferably include an aromatic tertiary amine derivative. Exemplary suitable hole-transporting materials are fully described by Y. Shirota in *J. Mater. Chem.*, 10, 1-25 (2000) and are illustrated as follows:

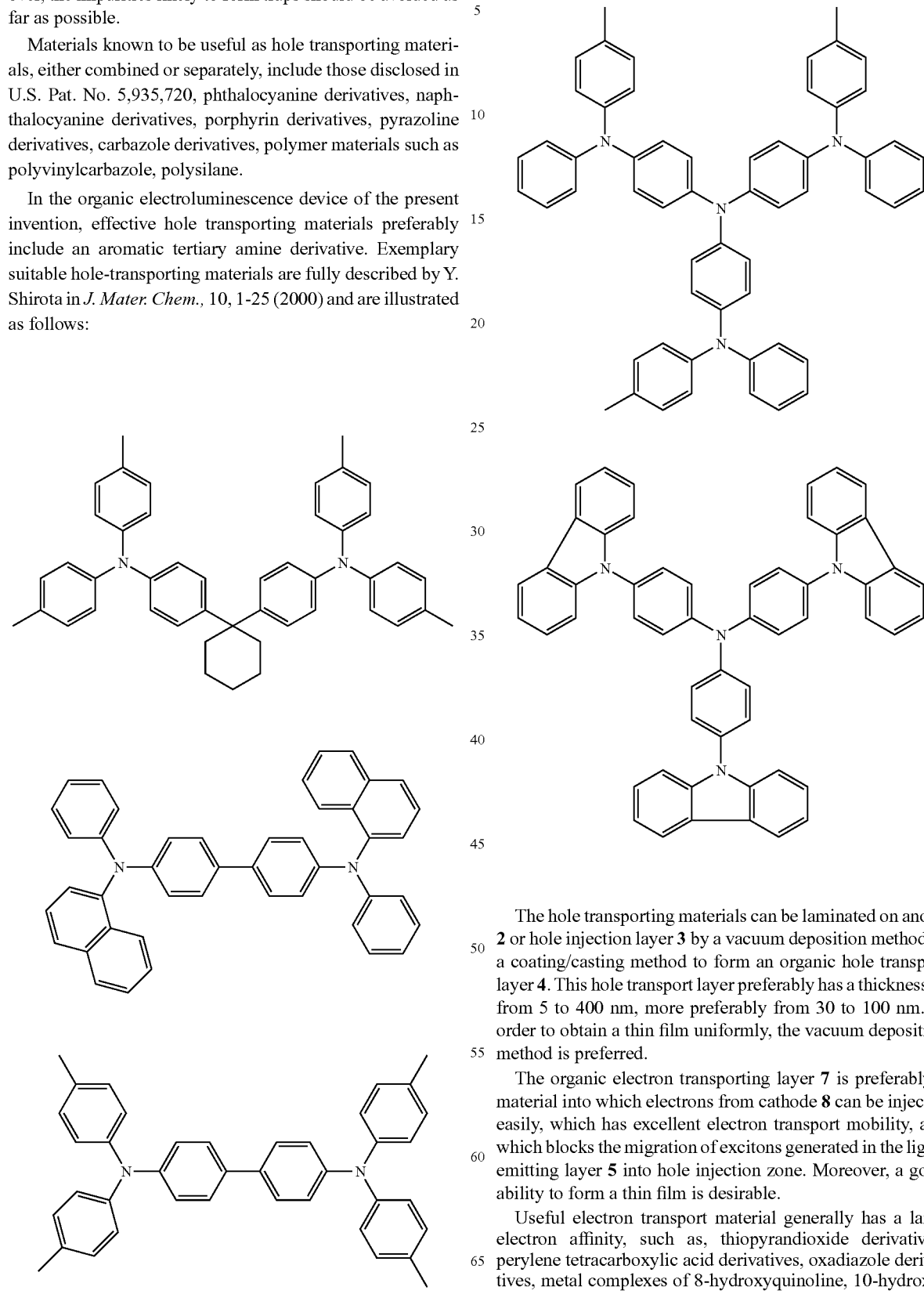

-continued

The hole transporting materials can be laminated on anode 2 or hole injection layer 3 by a vacuum deposition method or a coating/casting method to form an organic hole transport layer 4. This hole transport layer preferably has a thickness of from 5 to 400 nm, more preferably from 30 to 100 nm. In order to obtain a thin film uniformly, the vacuum deposition method is preferred.

The organic electron transporting layer 7 is preferably a material into which electrons from cathode 8 can be injected easily, which has excellent electron transport mobility, and which blocks the migration of excitons generated in the light-emitting layer 5 into hole injection zone. Moreover, a good ability to form a thin film is desirable.

Useful electron transport material generally has a large electron affinity, such as, thiopyrandioxide derivatives, perylene tetracarboxylic acid derivatives, oxadiazole derivatives, metal complexes of 8-hydroxyquinoline, 10-hydroxybenzo[h]quinoline, pyrrolopyridine derivatives, naphthylidine derivatives. Several examples, which are also disclosed by Y. Shirota in *J. Mater. Chem.*, 10, 1-25 (2000), and Chen, Shi and Tang in *Macromol. Symp.*, 125, 1 (1997), are illustrated as follows:

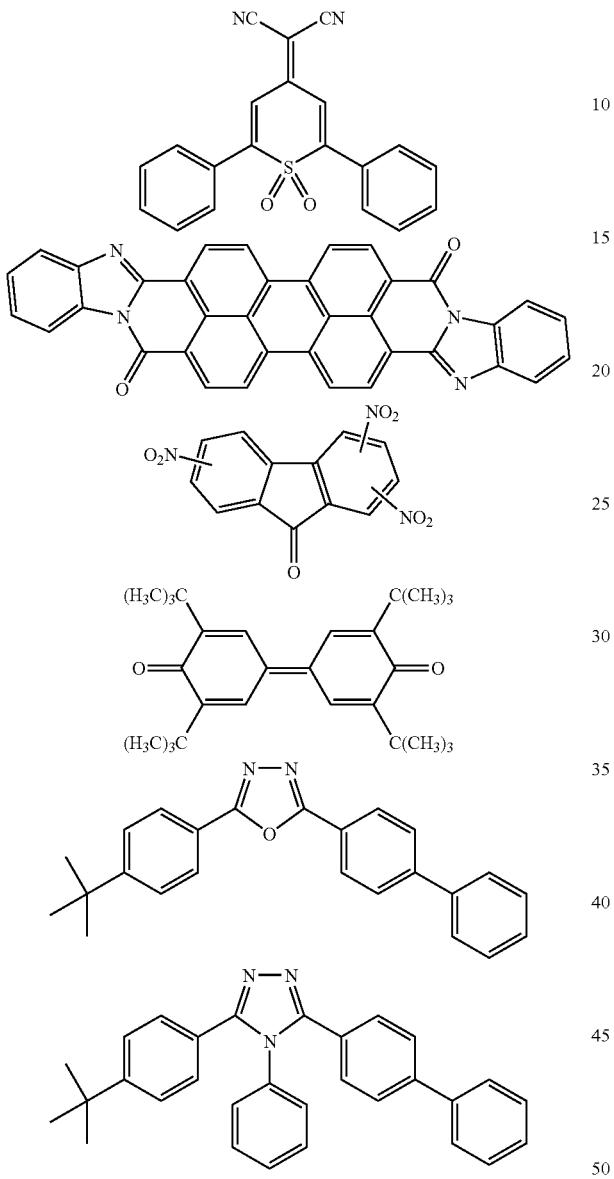

Electron transport layer 7 can be formed by a vacuum deposition method or a coating/casting method. This electron transport layer 7 usually has a thickness of from 5-400 nm, preferably from 30-100 nm. In order to obtain a thin film uniformly, the vacuum deposition method is preferred.

The hole blocking layer 6 preferably comprises a material which possesses a good ability to form uniform vacuum sublimed thin films, and exhibits a large ionization potential. By using the hole blocking materials, the hole can be blocked to transport into the electron transport layer further, so that the recombination zone can be refined, ultimately the EL performance can be improved. Materials known to be useful as hole blocking materials, either combined or separately, include BCP and TPBI, as well as those disclosed in by U. Mitschke and P. Bauerle in *J. Mater. Chem.*, 10, 1471-1507 (2000), exemplary illustrated as follows:

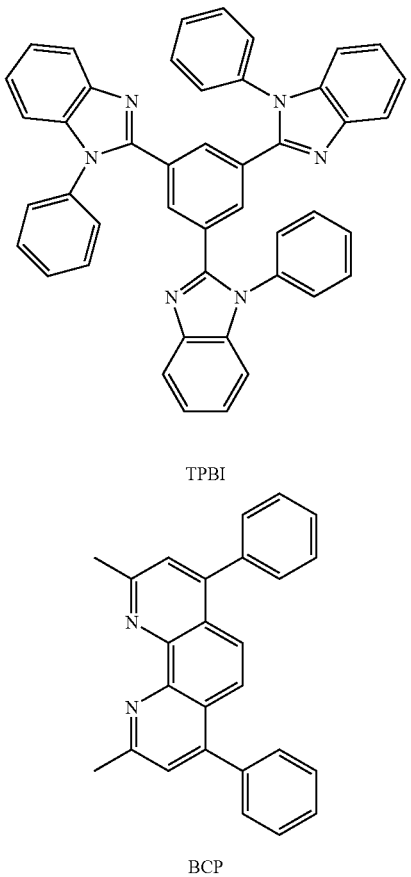

The organic light-emitting layer 5 of the present invention comprises a light-emitting material wherein electroluminescence is produced as a result of electron-hole recombination in this region. This electron-hole recombination produces excitons, which may decay to the ground state in a radiative way, resulting in an emission—fluorescence or phosphorescence. The light emitting materials is generally required to have a high emission quantum yield, a suitable energy gap, as well as a good ability to form a thin film uniformly. Materials for the emitting layer include the fused aromatic compounds, 8-hydroxyquinolinato metal complexes, such as $Alq_3$, substituted carbazole derivatives, as well as other fluorescence or phosphorescence dyes.

As mentioned above, doping a strong luminescent material into one of the host emitting materials mentioned above can improve the performance of an organic EL device. This method is believed to have the following advantages:

(i). Electroluminescent efficiency may be improved;

(ii) Color can be tuned by doping different emitting materials;

(iii) Emitting materials with poor ability to form film and concentration self-quenching can also be used; and (iv) The stability of an organic EL device can be improved.

Unlike the hosts for fluorescent emitters, the triplet energy levels in the host and the absorption of the guest triplet state are frequently unknown and, moreover, are difficult to quantify, optimizing guest-host systems for resonant triplet transfer is problematic. Comparisons of the absorption of the guest and the emission spectrum of the host are relevant only to the transfer of singlet states, but may nevertheless give a general indication of the likelihood for triplet transfer. Although some phosphorescent guests may trap charge and form excitons directly, it is likely that if host emission is to be avoided, then some form of energy transfer to the guest is necessary. Based on this assumption, the blue (400 nm peak emissive material 4,4'-N,N'-dicarbazole biphenyl CBP) was chosen as the host for triplet emitters. Furthermore, to maximize performance, electrophosphorescent devices should employ a conductive host material with a phosphorescent guest sufficiently dispersed to avoid "concentration quenching."

Accordingly, in the present invention, organic light emitting layer 5 comprises a multi-component material containing a host emitting material, such as one of those listed above, and a dopant (guest). It should be noted that the multi-component material of layer 5 may also be the hole transport material or the electron transport material, instead of a separated emission layer.

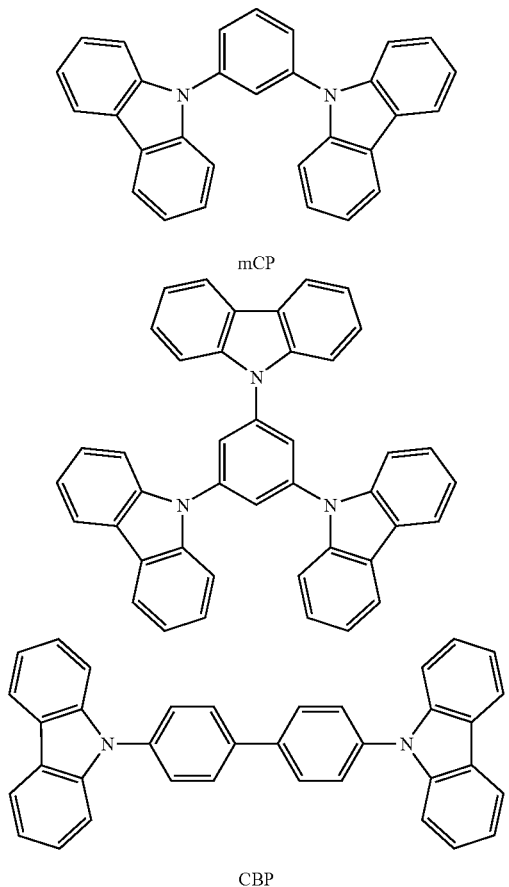

mCP

CBP

Of the host emitting materials listed above, the well-known host emitting material, (CBP), is particularly suitable for use as the host in the present organic light emitting layer 5. However, it should be noted that the EL device of the present invention is not limited to the use of CBP, and other hosts, such as those listed above, may be used instead.

As for the dopants for the host CBP, Applicants have found that the above-disclosed Ir-complexes with formulae [I]-[III] are capable of improving the efficiency and performance. In formulae [I]-[III], each $R_1$-$R_6$ is independently hydrogen, halogen, cyano, nitro, alkyl, alkylamino, dialkylamino, arylamino, diarylamino, haloalkyl containing a lower alkyl, hydroxyalkyl containing a lower alkyl, styryl, alkyloxy, alkylthio, aryloxy, arylthio, siloxy, aryl or substituted aryl, substituted or unsubstituted heterocycle.

Molecular structures for especially exemplary dopant used in the present invention are as follow:

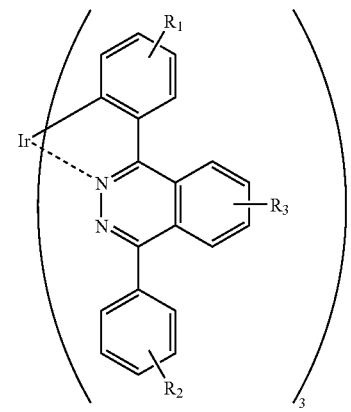

IrBPPa

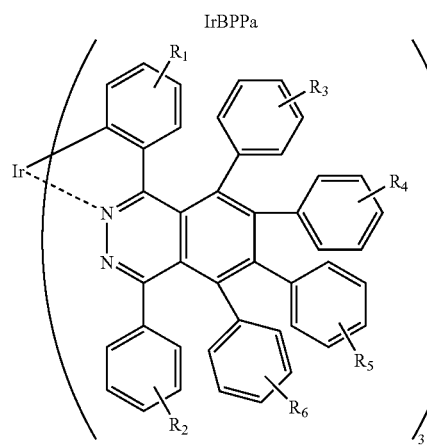

Ir-C$_2$

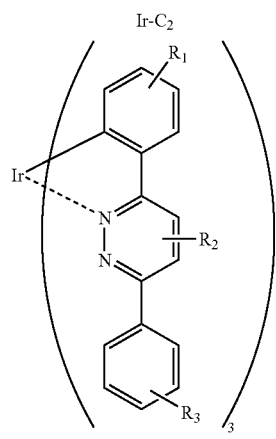

Ir-C$_3$

EXAMPLES

The present invention will be explained in more detail with reference to examples. It should be noted that the examples included below are illustrative purposes only, and that the invention is in no way limited to the embodiments used in the examples.

Unless otherwise indicated, the reactants and reagents used in the reactions described below are readily available materials. Such materials can be conveniently prepared in accordance with conventional preparatory procedures or obtained from commercial sources.

Example 1

Synthesis of 1,4-Bis(phenyl)phthalazine

To a cooled solution of 1,2-bis(benzoyl)benzene (286.32, 0.5 g, 1.75 mmol) in glacial acetic acid (12 ml) was added hydrazine monohydrate (3.5 mL) dropwise. The reaction mixture was refluxed for 4 hours. The resulting bright brown solution was added with water to produce pale yellow precipitate, yield 100%. This was used to the next reaction for complex without further purification. MS: m/z 283.0 (M+).

Example 2

Synthesis of Ir-Complex (Ir-BPPa)

1,4-bis(phenyl)phthalazine (FW=282.34, 370 mg, 1.34 mmol) and Ir(acac)$_3$ (FW=489.54, 164.3 mg, 0.336 mmol) were dissolved in degassed glycerol (10 ml). The reaction mixture was refluxed (220° C.) under nitrogen for 10 hours. Purple color precipitates turned out gradually during reflux. After reaction, the crude product was collected by filtration, washed with hexane and ether, dried in a vacuum (yield: 57%). It was then purified by flash-chromatographed on a silica gel column using dichlormethane as eluent. Addition of methanol to the solution followed by heating to boiling to evaporate dichloromethane resulted in precipitation of the product as dark-red color shining particles (40% yield). Melting point: 385.3° C.; $^1$H NMR: (Chloroform-d, 300 MHz) δ: 8.81 (d, 3H), 8.14 (d, 3H), 7.91 (d, 3H), 7.71 (t, 3H), 7.66 (m, 6H), 7.12 (m, 9H), 6.87 (t, 6H), 6.78 (d, 6H); MS: m/z (%) 1037.0 (100, M$^+$), 755 (15, M$^+$-BPPa); Calc. For C$_{60}$H$_{39}$N$_6$Ir (FW=1036.32): Calcd C, 69.50%; H: 3.76%, N: 8.11%; Found: C: 69.30%, H: 3.84%, N: 8.50%; UV-vis [λ/nm (ε/cm$^{-1}$M$^{-1}$)]: CH$_2$Cl$_2$, 231 (79520), 258 (48300), 316 (41250), 381-458 (11890), 521-529 (4500).

Example 3

The Procedure of Electroluminescence Device Fabrication

An indium-tin-dioxide (ITO) coated glass substrate was sequentially untrasonicated in a detergent, rinsed in deionized water and exposed to UV light for 20 minutes, dried. A hole transporting layer of N,N'-bis-(1-naphthyl)-N,N'-diphenyl-benzidine was deposited on ITO anode at the vacuum deposition rate about 15 nm/min. by using a tantalum boat to form a thickness of 60 nm. A light-emitting layer of CBP doped with a material with formula [I], [II], [III] was then co-deposited onto the hole-transporting layer with a thickness about 30 nm. The concentration of dopants can be controlled by deposition rate according to the requirement. At the following step, a hole blocking layer of TPBI was deposited onto the light-emitting layer with a thickness about 30 nm. An electron-transporting layer of AlQ$_3$ was deposited onto the light-emitting layer with a thickness about 30 nm Then, a cathode consisted of a 10/1 atomic ratio of Mg/Ag was deposited onto the AlQ$_3$ layer with a thickness about 200 nm. Finally, the device was hermetically packaged in a dry glove box.

Example 4

For the device fabrication, CBP, 4,4'-dicarbazolyl-1,1'-biphenyl, was used as the host for the red phosphorescent material Ir-BPPa. The doped CBP layer was interposed between a hole transport layer of NPB, 4,4'-di-1-naphythyl-N,N'-diphenyl-biphenyl-4,4'-diamine, and an electron transport layer of AlQ$_3$, tris(8-hydroxyquinolinato)aluminum(III). To prevent hole from drifting out of the doped CBP layer, a hole blocking layer, TPBI, 1,3,5-tri(phenyl-2-benzimidazolyl)-benzene was inserted between the CBP and AlQ$_3$ layers. The devices emitted pure red color at low driving voltage. However, at high driving voltage, due to recombination in the NPB layer in this kind of device structure, a very small amount of blue emission (440 nm) appears. The radiative energy of the blue part can be converted to red by inserting a thin layer of 0.5% IrBBPa-doped NPB layer. With the device configuration of ITO (30Ω/□)/NPB (15 nm)/NPB:0.5%IrBBPa (5 nm)/CBP: 5%IrBBPa (20 nm)/TPBI (10 nm)/AlQ$_3$ (40 nm), very high performance of red phosphorescence was achieved, Besides the high efficiency, another surprising feature of this device is that it gave the most saturated red color among all reported Ir complexes, and the CIE color coordinates (x=0.69, y=0.30) remain constant over a wide range of driving voltages from 0 to 15 V. The device had a maximum external efficiency of 8.43%, a current efficiency of 3.0 cd/A at a driving voltage of 6.5 V. Even at high current density of 200 mA/cm$^2$, the efficiency of the device remained high at 4.24% and 1.7 cd/A at 13.5 V.

TABLE 1

Summary of Ir-complex based red OLEDs in literature

| | No. | | | |
|---|---|---|---|---|
| | 1[1] | 2[2] | 3[3] | 4[4] |
| peak wavelength (nm) | 617 | | | 652.00 |
| CIE-x | 0.68 | 0.68 | 0.63 | 0.69 |
| CIE-y | 0.33 | 0.32 | 0.37 | 0.30 |
| Eff. % (cd/A) at 1 mA | 6.6 | | | 8.43 (3.0) |
| Eff. % (cd/A) at 10 mA | 6 | | | 7.0 (2.5) |
| Eff. % (cd/A) at 20 mA | | 8.46 | | 6.32 (2.35) |
| Eff. % (cd/A) at 100 mA | 4.6 | 9.21 | | 4.70 (1.91) |
| Eff. % (cd/A) of Maximum | 7 | 9.71 | 9.5 | 8.43 (3.0) |

[1]Lamansky, S; Djurovich, P.; Murphy, D.; Abdel-Razzaq, F.; Lee, H. -E.; Adachi, C.; Burrows, P. E.; Forrest, S. R.; Thompson, M. E. J. Am. Chem. Soc. 2001, 123, 4304.
[2]Su, Y. -J.; Huang, H. -L.; Li, C. -L.; Chien, C. -H.; Tao, Y. -T.; Chou, P. -T.; Datta, S.; Liu, R. -S. Adv. Mater. 2003, 15, 884.
[3]Duan, J. -P.; Sun, P. -P.; Cheng, C. -H. Adv. Mater. 2003, 15, 224.
[4]Present patent specification.

What is claimed is:

1. A compound according to the following formula:

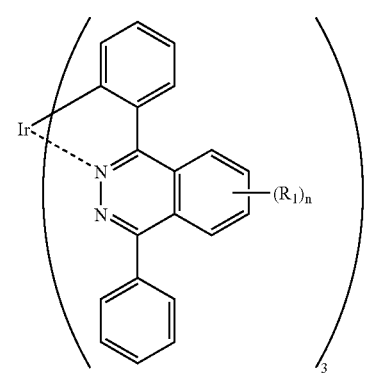

wherein R$_1$ is a phenyl group and n=0 to 4.

2. A compound according to claim 1, wherein n is 0 and the corresponding compound is:
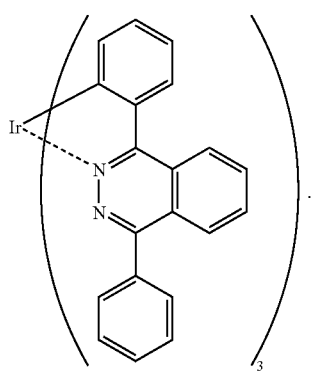
3. A compound according to claim 1, wherein n is 4 and the corresponding compound is:
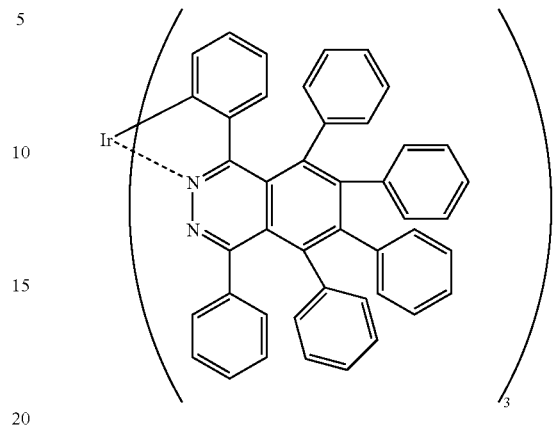
* * * * *